United States Patent
Zamosky

[11] Patent Number: 5,158,531
[45] Date of Patent: Oct. 27, 1992

[54] SPINAL ORTHOSIS

[75] Inventor: Gary Zamosky, 69 Freedman Ave., Nanuet, N.Y. 10954

[73] Assignees: Christina M. Zamosky; Gary Zamosky, both of Nanuet, N.Y.

[21] Appl. No.: 724,907

[22] Filed: Jul. 2, 1991

[51] Int. Cl.$^5$ .............................. A61F 5/02
[52] U.S. Cl. ............................ 602/19; 602/5
[58] Field of Search ............... 602/19, 5; 2/44, 45

[56] References Cited

U.S. PATENT DOCUMENTS

| | | |
|---|---|---|
| 245,655 | 8/1881 | Phelps . |
| 709,055 | 9/1902 | Sheldon . |
| 1,812,529 | 6/1931 | Haulbrook . |
| 1,931,990 | 10/1933 | Massack . |
| 2,973,030 | 2/1961 | Matthewson . |
| 3,331,367 | 7/1967 | Hastings . |
| 4,120,297 | 10/1978 | Rabischong . |
| 4,202,327 | 5/1980 | Glancy .................. 602/19 |
| 4,230,101 | 10/1980 | Gold ..................... 602/19 |
| 4,559,933 | 12/1985 | Batard et al. ............ 602/19 |
| 4,688,558 | 8/1987 | Hooper, Jr. et al. ....... 602/19 |
| 4,820,221 | 4/1989 | Aubrey . |
| 5,012,798 | 5/1991 | Graf et al. .............. 602/19 |
| 5,072,725 | 12/1991 | Miller ................... 602/19 |
| 5,074,288 | 12/1991 | Miller ................... 602/19 |

Primary Examiner—Stephen R. Crow
Assistant Examiner—Linda C. M. Dvorak
Attorney, Agent, or Firm—Stanley J. Yavner

[57] ABSTRACT

A spinal orthosis is provided with a continuous interior framework of ⅛" low density polyethylene, sandwiched between layers of ¼" thick aliplast, with an anterior opening to provide cosmetic acceptability and independence of the user for placing on and removing the orthosis. A floating abdominal apron is provided to cover the anterior opening and the orthosis is devoid of joints and hinges to accomplish flexion and extension.

4 Claims, 4 Drawing Sheets

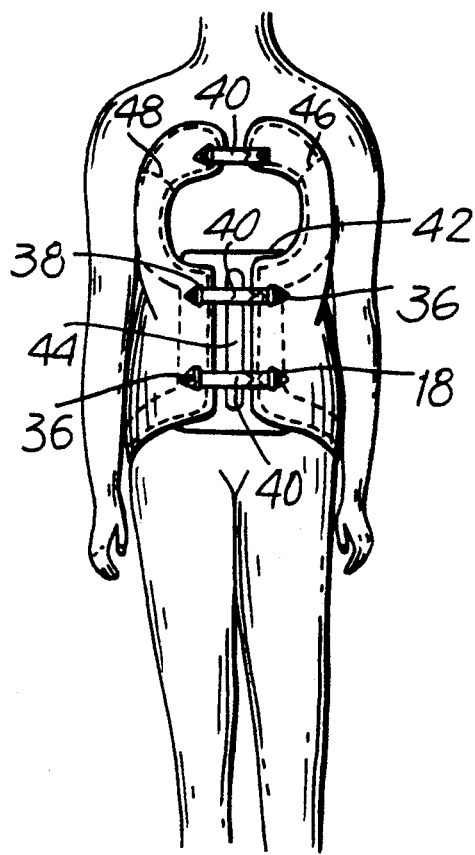 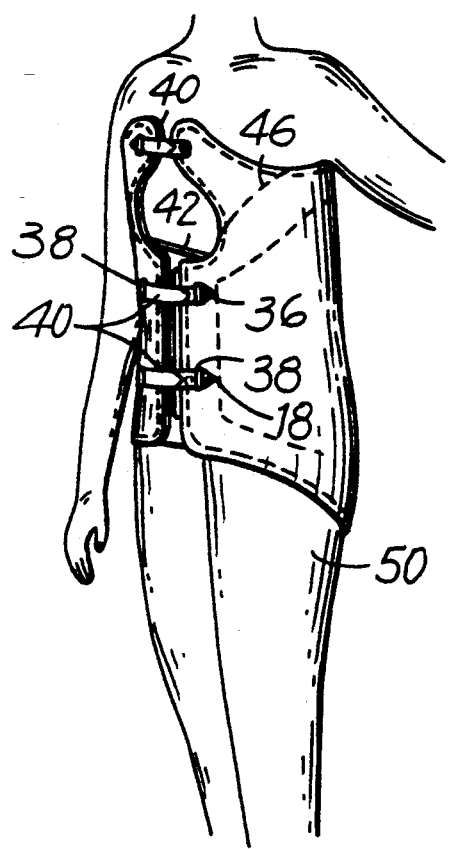

SPINAL ORTHOSIS

This invention relates primarily to spinal orthotic devices and more particularly to such devices for comfortably controlling body posture without rigidity, and with applicability to infants, juveniles, young adults and geriatric persons.

DESCRIPTION OF THE PRIOR ART AND BACKGROUND OF THE INVENTION

There are numerous devices marketed today, whose primary purpose is for body control, particularly for patients suffering from multiple sclerosis, cerebral palsy, other non-ambulatory impairments, scoliosis, respiratory insufficiency, pressure-sensitive skin, osteoporosis, pre and post operative conditions and arthritic problems.

Usually, however, such present-day devices lack flexibility, include rigid metallic portions, are ill-fitting, and do not allow for sufficient exposure of the skin to ambient conditions.

For instance, Aubrey U.S. Pat. No. 4,820,221, issued Apr. 11, 1989 relates to a lumbar support device for wearing about the torso of a user. The device is particularly intended for supporting the lumbar during water sports and is therefor made buoyant and quite rigid in the lumbar region.

Matthewson, U.S. Pat. No. 2,973,030, issued Feb. 28, 1961 discloses a non-continuous sheet metal frame; and Rabischong, et al, U.S. Pat. No. 4,120,297, issued Oct. 17, 1978 discloses a non-continuous frame of inflatable tubes.

Sheldon, U.S. Pat. No. 709,055, issued Sep. 16, 1902, Massack, U.S. Pat. No. 1,931,990, issued Oct. 24, 1933, Hastings, U.S. Pat. No. 3,331,367, issued Jul. 18, 1967, Phelps, U.S. Pat. No. 245,655, issued Aug. 16, 1881 and Haulbrook, Pat. No. 1,812,529, issued Jun. 30, 1931 also show non-continuous frameworks in brace construction, with a particularly complex arrangement being shown by the Phelps patent mentioned above.

SUMMARY OF THE INVENTION

Accordingly, a primary object of the present invention is to provide a spinal orthotic device, which is comfortable, allows freedom of movement for the wearer, and yet, controls body posture.

A further and more particular object of the present invention is to provide a spinal orthosis device which includes an anterior, abdominal opening and a continuous frame.

A still further object of the present invention is to provide such an orthosis device, with a structure that allows for flexion and extension of the torso, and without a metallic frame.

These and other objects of the present invention are provided in a spinal orthotic device which features a continuous, non-metallic frame, sandwiched between two layers of aliplast to allow particularly for rib expansion during respiration. Both the frame and the aliplast covering define an anterior, abdominal opening, in which there is placed a free- floating abdominal apron. Using this basic structure, various and variable sizes and shapes for spinal orthotic devices are enabled. Particularly, distal of the patient's sternal notch defined by the top anterior of the device, there is a cow-horn shaped section of aliplast and framework material, both removed when lumbar spinal support only is required.

BRIEF DESCRIPTION OF THE DRAWINGS

Other objects, features and advantages of the present invention will become apparent by the following, more detailed description of the preferred, but nonetheless illustrative, embodiment, with reference to the accompanying drawings, wherein:

FIG. 4 is a front view of the device of FIG. 3, but with cow-horn shaped additions at the top thereof;

FIG. 5 is a front and side isometric view showing particularly the device of FIG. 4, but with aliplast and frame material shown as removable to eliminate the cow-horn shaped sections, in order to enable lumbar spinal support in an alternative embodiment.

DETAILED DESCRIPTION OF THE PREFERRED AND ALTERNATIVE EMBODIMENTS

Figure 1:
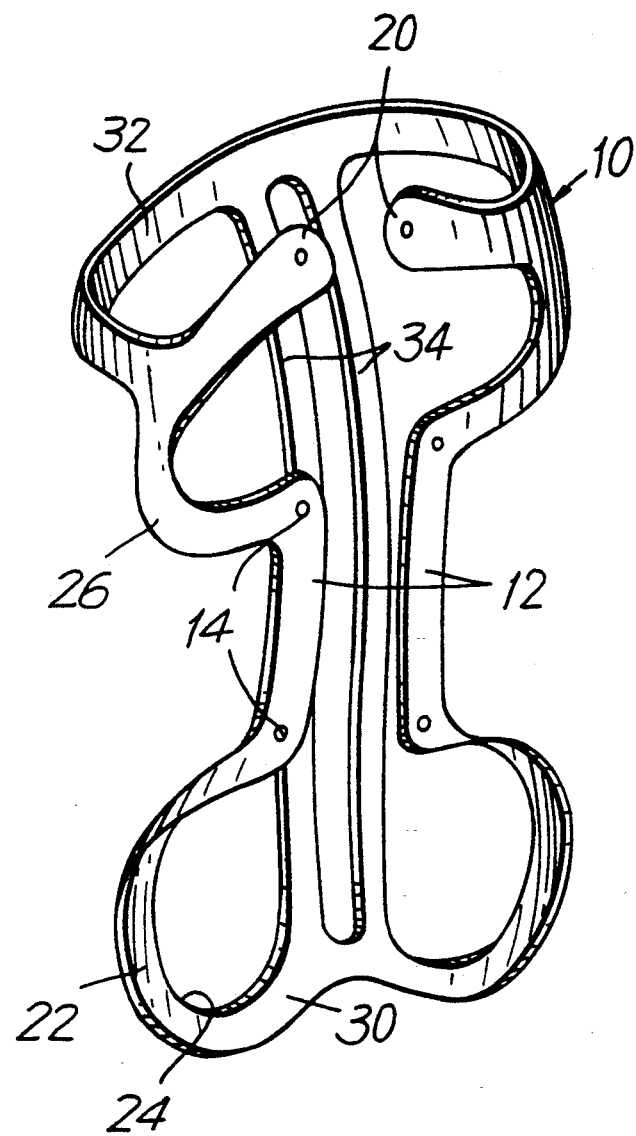
FIG. 1 is a front isometric view of the interior frame of the spinal orthotic device constructed according to the present invention.
Figure 3:
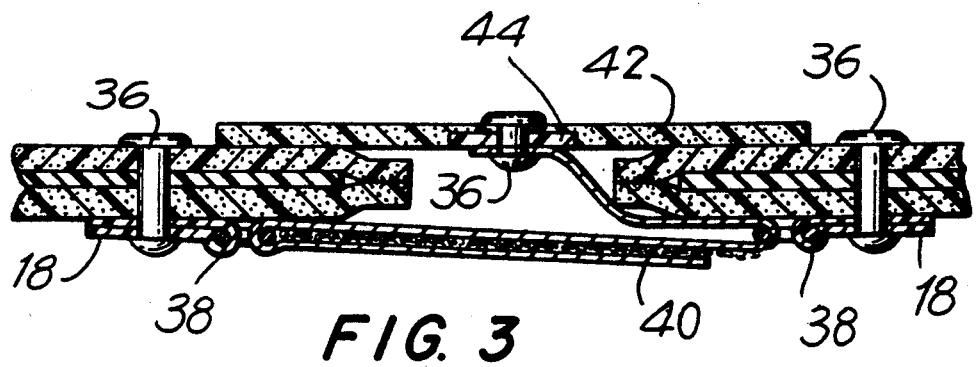
FIG. 3 is a sectional view, taken along the line 3—3 of FIG. 2, and showing assembly details of the invention.

Referring to the drawings, FIG. 1 shows an anterior view of the spinal orthotic device frame construction, according to the present invention. The frame, generally designated 10, includes a continuous and flexible formation of one-eighth inch low-density polyethylene plastic, defining therein mounting holes 14 to accommodate rivets for securely attaching outer layers of an aliplast coating 16 and plastic chafes 18, as will hereinafter be described (FIG. 3).

More specifically, frame 10 includes upper abdominal vertical portions 12, abdominal portions 22 defining abdominal opening 24, and breast portion 26. At the upper portion of frame 10, are cow-horn shaped sections 20 for encircling the upper chest portion of the patient.

The lower frame includes lower encircling portion 30; and likewise, the upper part of frame 10 includes upper frame encircling portion 32, both of which portions 30, 32 are connected by vertical struts 34, tracing generally the spinal column of the user.

Figure 2:
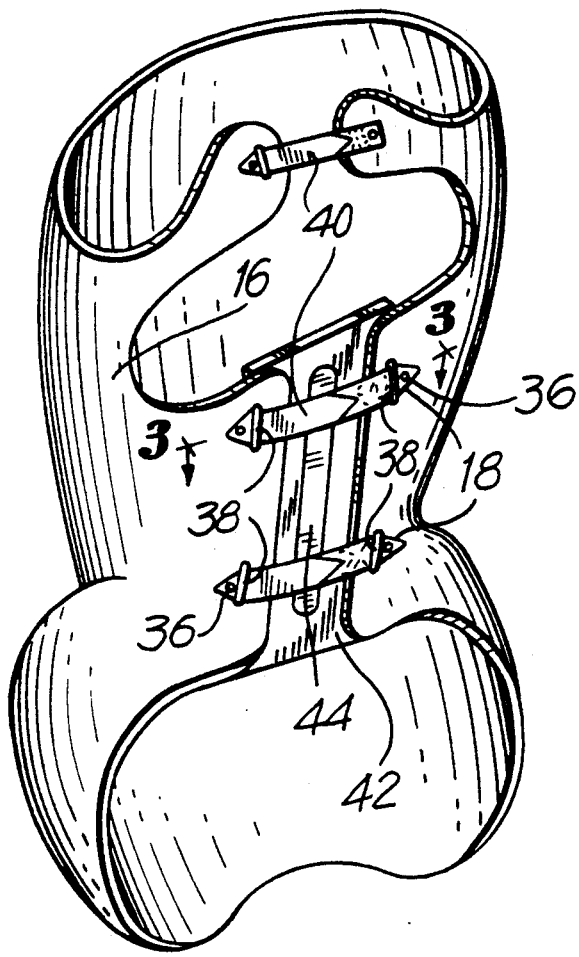
FIG. 2 is a left side and front isometric view of the spinal orthotic device according to the present invention, showing the frame of FIG. 1 sandwiched between aliplast layers, and with a free-floating abdominal plate attached thereto.

Referring to FIG. 2, the spinal orthosis is shown with frame 10 sandwiched between layers of aliplast 16 and with rivets 36 applied therethrough for securing one inch plastic chafes 18, having stainless steel loops 38 for, in turn, securing Velcro closures 40. In a preferred form of construction for the present invention, abdominal plate 42, free-floating, is used for insertion within abdominal opening 24 defined by portions 22, 12 in order to provide even more flexibility, and yet support, for the user-patient.

Abdominal plate 42 is formed of three-sixteenth inch aliplast 4E with a one-eighth inch thick polyethylene plate 44 to reinforce it. By rivets or the use of VELCRO fastening strips, or the like (not shown) on the reinforcing strip, attachment is thereby conveniently made, but with flexibility, between abdominal plate 42 and straps 40.

Referring to FIG. 4, an anterior view of the complete spinal orthosis is shown with its aliplast 4E covering, but with an indication at locations 46, 48 where "cow-horn" removal would enable lumbar spinal support only. Without removal, such cow-horn sections 20 would provide full spinal support for the patient in a position at least one-half inch below the sternal notch of the patient 50.

The FIG. 5 representation shows in more detail the lateral view of the overall construction, and particularly, the removal point 46 for use when lumbar spinal support only is desired for patient 50. In the alternative embodiment, with cow-horn sections 20 removable, a weakened area, with perforations or the like, at 46, 48 will enable the clinical construction variation (sections 20 removed) to be accomplished.

Figure 6:
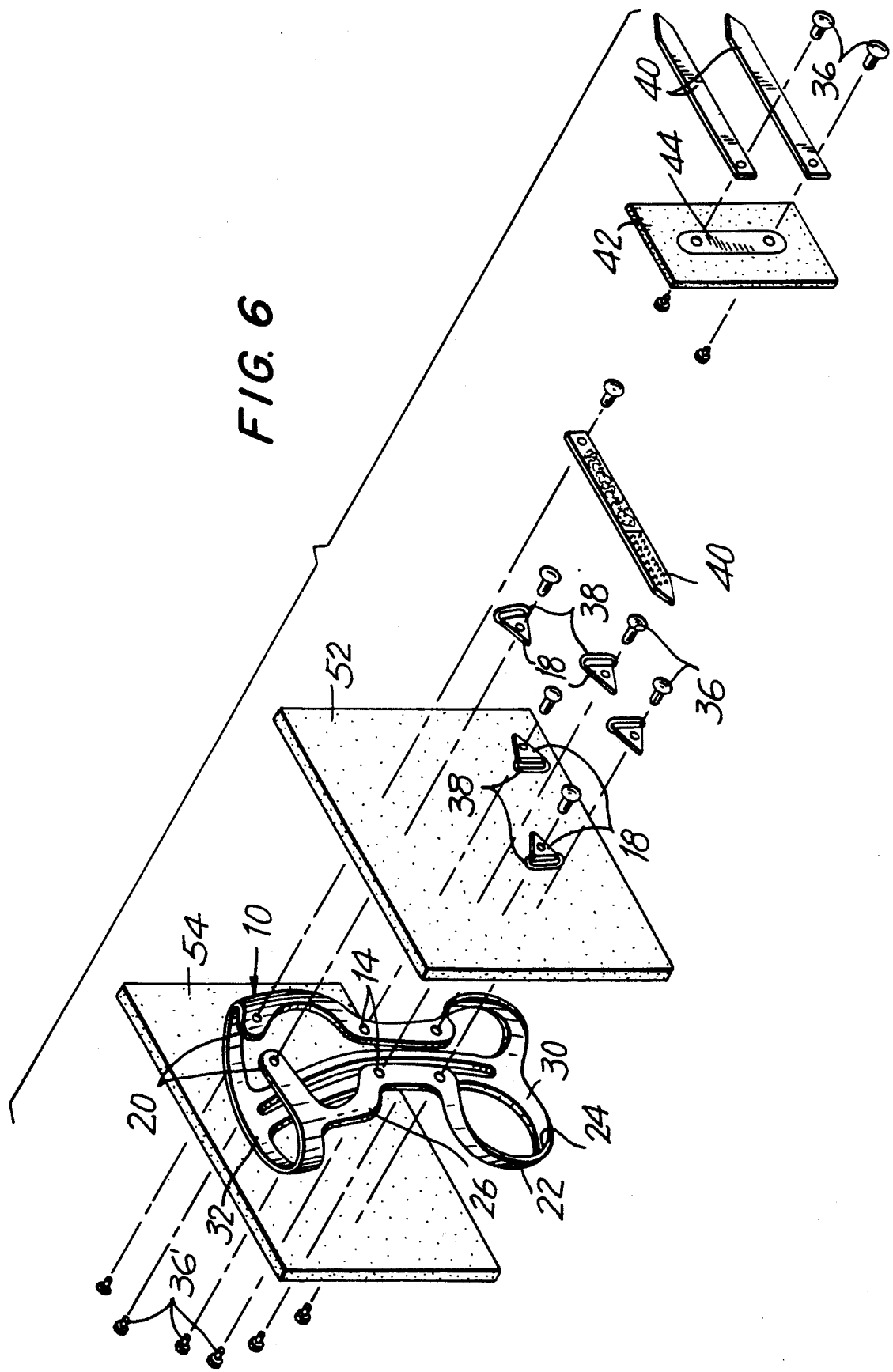
FIG. 6 is an exploded view of the various parts of a spinal orthotic device construction according to the present invention.

In order to provide a more complete description of the present invention, a series of assembly steps, by way of example only, is now provided, with reference to FIG. 6, in order to enable a more complete understanding of construction according to the present invention. Assuming that a full spinal support is desired, cow-horn sections 20, and a full frame 10 as described with reference to FIGS. 1 and 2 is provided. The material of frame 10 is low-density polyethylene plastic, approximately one-eighth inch thick and one to one and one-half inches wide, molded over a plastic model, with an inner layer of aliplast 4E and six one-eighth inch holes 14 pre-drilled. By manufacture in this manner, a continuous frame 10 is produced.

Sheet 52 of aliplast 4E, one-quarter inch thick, is heat-molded over a positive model and frame 10 is formed thereover. Thereafter, sheet 54 of aliplast 4E, one-quarter inch thick, is heat-molder over the frame and sheet 52, to thereby form an outer layer 54 and an inner layer 52, with frame 10 sandwiched therebetween. Plastic chafes 18 with stainless steel loops 38 are riveted by use of rivets 36 through mounting holes 14 into rivet bases 36'.

The floating abdominal plate or apron 42 is then formed of three-sixteenth inch aliplast 4E with reinforcing plate 44 attached; and the entire plate structure is then riveted (36") or otherwise attached to VELCRO closures 40, as shown in FIG. 6, in order to be properly arranged as shown in FIG. 3.

The foregoing description of a preferred and alternative embodiments of a spinal orthosis is provided to enable those skilled in the art to understand its structure and applicability; but limitations of this invention are to be imposed only by the following claims:

What is claimed is:

1. A spinal orthosis for providing comfort control, spinal support, and for allowing rib expansion during respiration of a user-patient, said spinal orthosis comprising:
    inner and outer layers of plastic material;
    a non-metallic continuous frame positioned between said layers and heat formed therewith;
    said frame and layers adapted and arranged to support and encircle the torso of the user-patient, and defining therein an abdominal opening;
    closure means for extending across said abdominal opening;
    a free-floating abdominal apron positioned within said abdominal opening; and
    means for flexibility attaching said apron to said closure means thereby allowing the user-patient to selectively position said apron with respect to said frame and layers so as to provide comfort control.

2. The spinal orthosis according to claim 1 wherein said frame further includes upper, cow-horn sections positioned above said abdominal opening and adapted to rest at least one-half inch below the sternal notch of the user-patient.

3. The spinal orthosis according to claim 1 wherein said closure means includes loops and chafes fixed to said frame.

4. The spinal orthosis according to claim 1 wherein said apron includes a reinforcing plate secured to said closure means.

* * * * *